US008568693B2

(12) United States Patent
Danikas et al.

(10) Patent No.: US 8,568,693 B2
(45) Date of Patent: Oct. 29, 2013

(54) THERAPY SELECTION METHOD

(75) Inventors: Antonios Danikas, Amersham (GB); Clifford Smith, Amersham (GB); Ian A Wilson, Amersham (GB)

(73) Assignee: GE Healthcare AS, Oslo (NO)

( * ) Notice: Subject to any disclaimer, the term of this patent is extended or adjusted under 35 U.S.C. 154(b) by 329 days.

(21) Appl. No.: 12/919,019

(22) PCT Filed: Feb. 26, 2009

(86) PCT No.: PCT/EP2009/052282
§ 371 (c)(1),
(2), (4) Date: Aug. 24, 2010

(87) PCT Pub. No.: WO2009/106566
PCT Pub. Date: Sep. 3, 2009

(65) Prior Publication Data
US 2011/0002849 A1    Jan. 6, 2011

(30) Foreign Application Priority Data
Feb. 26, 2008  (GB) .................................. 0803477.9

(51) Int. Cl.
*A61K 49/00* (2006.01)
(52) U.S. Cl.
USPC ............ 424/9.2; 424/1.11; 424/1.65; 424/9.1
(58) Field of Classification Search
USPC ........... 424/1.11, 1.49, 1.65, 1.73, 1.81, 1.85, 424/1.89, 9.1, 9.2, 9.3, 9.4, 9.5, 9.6; 514/1, 514/1.1; 534/7, 10–16; 530/300
See application file for complete search history.

(56) References Cited

FOREIGN PATENT DOCUMENTS

| EP | 1679082 | 7/2006 |
|---|---|---|
| WO | 02/087630 | 11/2002 |
| WO | 2005/058371 | 6/2005 |

OTHER PUBLICATIONS

Ross et al (The Oncologist, 1998, vol. 3, pp. 237-252).*
Safran H. et al.: "Trastazumab, Paclitaxel, Cisplatin, and Radiation for Adenoicarcinoma of the Esophagus: A Phase I Study" Cancer Investigation, vol. 22, No. 5, 2004, pp. 670-677.
Kiesslich et al: "In Vivo Histology of Barrett'S Esophagus and Associated Neoplasia by Confocal Laser Endomicroscopy" Clinical Gastroenterology and Hepatology, American Gastroenterological Association, US, vol. 4, No. 8, Aug. 1, 2006, pp. 979-987.
Waldmann S. A.: "Opportunities for Near-Infrared Thermal Ablation of Colorectal Metastases by Guanylyl Cyclase C-Targeted Gold Nanoshells" Future Medicine, vol. 2, No. 6, 2006, pp. 705-716.
Watson G A et al.: "Inhibition of C-Met as a Therapeutic Strategy for Esophageal Adenocarcinoma" Neoplasia, Neoplasia Press, Ann Arbor, MI, US, vol. 8, No. 11, Nov. 1, 2006, pp. 949-955.
Martins A. S. et al.: "Insuline-Like Growth Factor I Receptor Pathway Inhibition by ADW742, Alone or in Combination With Imatinib, Doxorubicin, or Vincristine, is a Novel Therapeutic Approach in Ewing Tumor" Clin Cancer Res, vol. 12, No. 11, 2006, pp. 3532-3540.
Nilsson, et.al. "Affibody (R) Molecules: New Protein Domains for Molecular Imaging and Targeted Tumor Therapy." Curr. Opin. Drig Disc. Dev. vol. 10 No. 2, 2007. pp. 167-175.
PCT/EP2009/052282 ISRWO dated Oct. 28, 2009.
GB 0803477.9 Search Report Jun. 26, 2008.

* cited by examiner

*Primary Examiner* — D L Jones
(74) *Attorney, Agent, or Firm* — Yonggang Ji

(57) ABSTRACT

The present invention relates to a method to assist in the determination of therapy for a patient suffering from Barrett's oesophagus, especially where first-line therapy has been unsuccessful and when dysplasia has been diagnosed. The method comprises the use of an imaging agent comprising a vector which targets (a) Her2, (b) cMet, (c) guanylyl cyclase or (d) IGF1R. The imaging agent is suitable for radioisotope or optical imaging in vitro or preferably in vivo.

12 Claims, 2 Drawing Sheets

FIG. 1

| | | |
|---|---|---|
| Barrett's no dysplasia | → • symptom control /PPI<br>• anti-reflux surgery | → endoscopy every 2 years |
| Indefinite for dysplasia | → re-evaluation (endoscopy) | → PPI → endoscopy at 6 months for re-classification |
| Low grade dysplasia | → Intensive PPI | → 6 monthly endoscopy → regression: manage as BO<br>persistence: • repeat PPI/ endoscopy<br>• consider endosc. mucosal ablation |
| High grade dysplasia | → • Surgical resection<br>• endoscopic mucosal ablation | → Life-long endoscopy (6 monthly) |
| Carcinoma | → Surgical resection +/- chemotherapy | → palliative care |

THERAPY SELECTION METHOD

This application is a filing under 35 U.S.C. 371 of international application number PCT/EP2009/052282, filed Feb. 26, 2009, which claims priority to Great Britain application number 0803477.9 filed Feb. 26, 2008, the entire disclosure of which is hereby incorporated by reference.

FIELD OF THE INVENTION

The present invention relates to a method to assist in the determination of therapy for a patient suffering from Barrett's oesophagus, especially where first-line therapy has been unsuccessful and when dysplasia has been diagnosed. The method comprises the use of an imaging agent comprising a vector which targets (a) Her2, (b) cMet, (c) guanylyl cyclase or (d) IGF1R.

The present invention also provides the use of the imaging agents and/or labelled vector in the method of the invention.

BACKGROUND TO THE INVENTION

Oesophageal cancer represents less than 5% of all reported cancer cases, but ca. 30,000 new such cases are diagnosed per annum in the USA and the survival rate is low (see below). Oesophageal cancer can be divided into two major types, squamous cell carcinoma and adenocarcinoma, depending on the type of cells that are malignant. Barrett's oesophagus is a pre-malignant condition which is associated with an increased risk of development of oesophageal cancer; especially adenocarcinoma [Kiesslich et al, Clin. Gastroenterol. Hepatol., 4, 979-987 (2006)]. Chronic reflux increases risk for Barrett's oesophagus, and it has therefore been suggested that gastro oesophageal reflux (GERD) is a risk factor for oesophageal cancer.

Adenocarcinoma of the oesophagus is more prevalent than squamous cell carcinoma in the USA and Western Europe. Oesophageal cancer can be a treatable disease but is rarely curable. The overall 5-year survival rate is between 5% and 30%. Early diagnosis of oesophageal cancer improves the survival rate of the patient. Primary treatment includes surgery alone or chemotherapy in combination with radiation. Chemotherapy used in treatment of oesophageal cancer includes 5-fluorouracil and cisplatin. Lack of precise pre-operative staging is a major clinical problem.

The presence of low grade dysplasia (i.e. abnormal tissue growth) in Barrett's oesophagus is a risk factor for the development of oesophageal cancer, but surveillance currently relies on histopathology [Lim et al, Endoscopy, 39, 581-7 (2007)]. Diagnosis of dysplasia in Barrett's oesophagus is currently via random four-quadrant biopsies every 1 to 2 cm (the Seattle protocol), which is time-consuming and costly [DaCosta et al, Best Pract. Res. Clin. Gastroenterol., 20(1), 41-57 (2006)]. Dysplasia in Barrett's oesophagus is not normally visible during routine endoscopy [Endlicher et al, Gut, 48, 314-319 (2001)].

U.S. Pat. No. 6,035,229 (Washington Research Foundation) describes a system for detecting Barrett's oesophagus utilizing an illumination and imaging probe at the end of a catheter. The document does not disclose an optical contrast agent.

Staining of Barrett's oesophagus tissue in vivo has been compared with staining of biopsy samples in vitro, using the dye methylene blue in the detection of highly dysplastic or malignant tissue [Canto at al, Endoscopy, 33, 391-400 (2001)].

Kiesslich at al [Clin. Gastroenterol, Hepatol., 4, 979-987 (2006)] reported on the use of fluorescein to aid the detection of Barrett's epithelium and associated neoplasia using confocal laser endomicroscopy.

WO 2005/058371 discloses optical imaging contrast agents for imaging of oesophageal cancer and Barrett's oesophagus in vivo. The contrast agents have an affinity for a biological target which is abnormally expressed in Barrett's oesophagus.

The contrast agents of WO 2005/058371 are preferably of formula:

V-L-R where:
V is one or more vector moieties having affinity for an abnormally expressed target in oesophageal cancer or Barrett's oesophagus;
L is a linker moiety or a bond; and
R is one or more reporter moieties detectable in optical imaging.

A wide range of targets is described, but the target is preferably selected from E-cadherin, CD44, P62/c-myc (HGF receptor), p53 and EGFR/erB-2. The vector (V) is stated to be preferably selected from peptides, peptoid moieties, oligonucleotides, oligosaccharides, fat-related compounds and traditional organic drug-like small molecules. The reporter (R) is preferably a dye that interacts with light in the wavelength region from the ultraviolet to the near-infrared part of the electromagnetic spectrum.

Barrett's Oesophagus is a condition characterised by replacement of squamous oesophageal epithelium with columnar epithelium (metaplasia). A proportion of Barrett's Oesophagus patients will develop oesophageal adenocarcinoma, and the critical step in this process is the formation of dysplasia. Therefore patients diagnosed with dysplasia undergo therapy which can include anti-reflux medication, endoscopic mucosal ablation and surgical resection, depending on the severity of the disease (FIG. 1; summarised from "Guidelines for the Diagnosis and Management of Barrett's Columnar-lined Oesophagus", UK Society of Gastroenterology, August 2005; www.bsg.org.uk):

Treated patients are followed up at 6 monthly intervals to assess response to therapy. Responders (i.e. patients where the evidence is that the therapy is being effective), are treated as low-risk patients, while continued/additional treatment is considered for non-responders. There is a need for better therapy selection, especially among Barrett's Oesophagus patients that do not respond to first-line treatment, since more target specific therapies are being developed.

The Present Invention.

The present invention relates to a method to assist in the determination of therapy for a patient suffering from Barrett's oesophagus. The method comprises the use of an imaging agent comprising a vector which targets (a) Her2, (b) cMet, (c) guanylyl cyclase or (d) IGF1R. The method provides a therapy selection tool, of particular value for patients that do not respond to first-line treatment. Patients that are shown to strongly express one of these markers in the diseased tissue are expected to benefit from therapies which targeting those cellular proteins (FIG. 2).

The present invention provides evidence that cMet, Her2, IGF1-R and guanylyl cyclase c expression increases in subpopulations of Barrett's patients. Hence, identification of such patients using suitable imaging agents targeted to these proteins would allow those subpopulations to benefit from cMet, Her2, IGF1-R or guanylyl cyclase c targeted drug therapies, and at the same time enable more effective use of therapy resources.

BRIEF DESCRIPTION OF THE FIGURES

FIG. 1 illustrates the present guidelines for management of Barrett's patients.

DETAILED DESCRIPTION OF THE INVENTION

Figure 2:
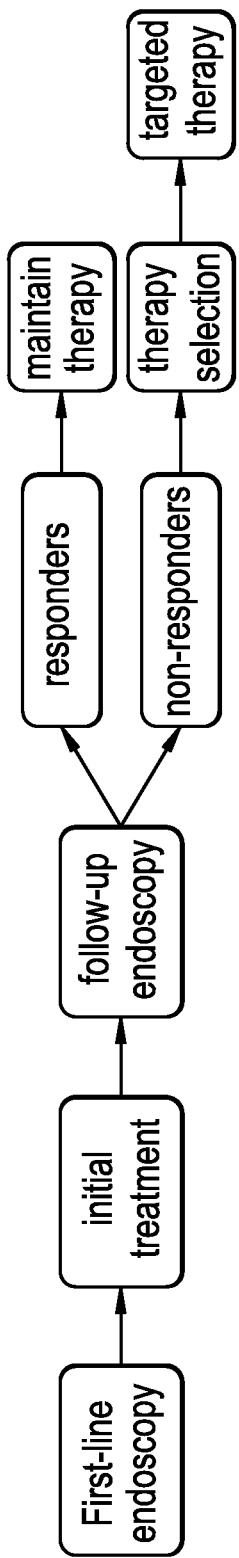
FIG. 2 is a scheme that illustrates how therapy selection fits within the patient management scheme.

In a first aspect, the present invention provides a method to assist in the determination of the most suitable course of therapy for an individual patient previously diagnosed to be suffering from Barrett's oesophagus, said method comprising:
  (i) provision of an imaging agent which comprises a vector which selectively targets a protein marker chosen from one of (a) Her2, (b) cMet, (c) guanylyl cyclase C or (d) IGF1R, said vector being labelled with an imaging moiety, wherein said imaging moiety is chosen from a radioisotope or an optical reporter;
  (ii) imaging at least a portion of the oesophagus of said patient with a first imaging agent from step (i):
  (iii) making a determination from the imaging of step (ii) whether there is increased uptake of the imaging agent relative to background at one or more locations of the patient's oesophagus;
  (iv) when the determination of step (iii) shows abnormal uptake, the appropriate targeted therapy for the patient is determined by the protein marker of the imaging agent used in step (ii):
    (a) for Her2, treatment with a drug or therapy which targets Her2;
    (b) for cMet, treatment with a drug or therapy which targets cMet;
    (c) for guanylyl cyclase C, treatment with a drug or therapy which targets guanylyl cyclase C;
    (d) for IGF1R, treatment with a drug or therapy which targets IGF1R;
  (v) when the determination of step (iii) is normal, the targeted therapy determined under step (iv) is determined to be unsuitable for that individual patient, and either a different therapy is given to said patient, or steps (iii)-(v) are repeated for said patient with a second imaging agent which comprises a different vector to that employed in step (ii).

By the term "previously diagnosed" is meant that the patient has already been diagnosed as suffering from Barrett's Oesophagus, or is suspected to be suffering from Barrett's Oesophagus. The diagnosis would have been made on the basis of clinical symptoms plus typically confirmation using first-line endoscopy. Such first line endoscopy is currently carried out with white light, in order to collect random, four quadrant biopsies. Histological assessment of these biopsies confirms the degree of disease.

By the term "imaging agent" is meant a compound suitable for imaging the mammalian body in vivo or for imaging biopsy samples taken from the mammalian body in vitro. Preferably, the mammal is a living human subject. The in vivo imaging may be invasive (eg. intra-operative or endoscopic) or non-invasive. A preferred in vivo imaging method is endoscopy.

By the term "selectively targets" is meant that the vector has a substantially higher affinity for the target compared to background tissue, and other potential targets. The vector is able to bind to the target with high affinity (with a Ki value in the range 0 to 50 nM, preferably sub-nM i.e less than 1.0 nM).

The terms Her2, cMet, guanylyl cyclase C and IGF1R have their conventional meanings. Further description is as follows:

Her2 is also known as erbB-2. Her2 is a member of the epidermal growth factor receptor family. It is a 185 kDa cell membrane surface-bound receptor tyrosine kinase and is involved in signal transduction pathways associated with cell growth and differentiation.

The cMet receptor is a high affinity receptor for hepatocyte growth factor/scatter factor (HGF/SF), a disulfide-linked heterodimeric molecule produced predominantly by mesenchymal cells and acting primarily on cMet-expressing epithelial cells in an endocrine and/or paracrine fashion.

Guanylyl cyclase C (GCC) is a member of the guanylyl cyclase receptors with a role in control of fluid secretion in epithelial cells of the lower GI tract. It is a 123 kDa brush border membrane protein encoded by the GUCY2C gene (12p12) and consists of a extracellular ligand binding domain, a single transmembrane spanning region, and a cytoplasmic domain.

The insulin-like growth factor receptor (IGF-1R, gene location 15q25) is a 155 kDa transmembrane heterotetramer with a significant role in regulation of cell survival, proliferation as well as cell-cell adhesion. It consists of two extracellular $\alpha$ and two transmembrane $\beta$ subunits. The $\alpha$ subunits contain the binding domain for IGF-1 while the intracellular part of the $\beta$ subunits contain tyrosine kinases for autophosphorylation and initiation of signalling. IGF1-R has 60% sequence homology to the insulin receptor. Similarly, its main ligand, IGF-1 has 50% homology to insulin, although the downstream signalling pathways are not common.

Radioisotopes suitable for in vivo imaging may be metals or non-metals, and are positron emitters for Positron Emission Tomography (PET) imaging, or gamma-emitters for Single Photon Emission Computer Tomography (SPECT). When the imaging moiety is a radioactive metal ion, i.e. a radiometal, suitable radiometals can be either positron emitters (for PET imaging) such as $^{64}$Cu, $^{48}$V, $^{52}$Fe, $^{55}$Co, $^{94m}$Tc or $^{68}$Ga; or $\gamma$-emitters (for SPECT imaging) such as $^{99m}$Tc, $^{111}$In, $^{113m}$In, or $^{67}$Ga. Preferred radiometals are $^{99m}$Tc, $^{64}$Cu, $^{68}$Ga and $^{111}$In. Most preferred radiometals are $\gamma$-emitters, especially $^{99m}$Tc. When the imaging moiety is a gamma-emitting radioactive halogen (for SPECT imaging), the radiohalogen is suitably chosen from $^{123}$I, $^{131}$I or $^{77}$Br. A preferred gamma-emitting radioactive halogen is $^{123}$I. When the imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

Suitable radioisotopes suitable for in vitro imaging of biopsy samples taken from the patient are known in the art, and include $^{125}$I, $^{3}$H, and $^{14}$C.

When the imaging moiety is an optical the reporter is any moiety capable of detection either directly or indirectly in an optical imaging procedure. The reporter might be a light scatterer (eg. a coloured or uncoloured particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most preferably the reporter has fluorescent properties.

Preferred organic chromophoric and fluorophoric reporters include groups having an extensive delocalized electron system, eg. cyanines, merocyanines, indocyanines, phthalocyanines, naphthalocyanines, triphenylmethines, porphyrins, pyrilium dyes, thiapyriliup dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Particular examples of chromophores which may be used include: fluorescein, sulforhodamine 101 (Texas Red), rhodamine B, rhodamine 6G, rhodamine 19, indocyanine green, the cyanine dyes Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Floor 633, Alexa Fluor 647, Alexa Fluor 660, Alexa Fluor 680, Alexa Fluor 700, and Alexa Fluor 750.

Particularly preferred are dyes which have absorption maxima in the visible or near infrared region, between 400 nm and 3 µm, particularly between 600 and 1300 nm. Optical imaging modalities and measurement techniques include, but not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarisation, luminescence, fluorescence lifetime, quantum yield, and quenching.

For steps (iv) and (v), increased uptake relative to background indicates the presence of the protein marker (a)-(d) of step (i), since healthy background oesophageal tissue (squamous) expresses no or low levels of such markers. This indicates that the targeted therapy of step (iv) could be of value.

Vectors suitable for Her2 binding include the antibodies Trastuzumab (Herceptin™, Genentech) and Pertuzumab (Omnitarg™, Genentech. These have been reviewed by Pal or al [Rev. Endocr. Metab. Disord., 8, 269-277 (2007)]. Affibodies with specific affinity for Her2 have also been described—see eg. Nilsson et al [Curr. Opin. Drug Disc. Dev., 10, 167-175 (2007)].

Vectors suitable for cMet binding include cyclic peptides of 17 to 30 amino acids which comprises the amino acid sequence (SEQ-1):

Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$;

wherein X$^1$ is Asn, His or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds;

Preferred such peptides are of SEQ-2 or SEQ-3:
(SEQ-2) Ser-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$;
(SEQ-3) Ala-Gly-Ser-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$-Gly-Thr.

Especially preferred such peptides have X$^3$ equal to Arg. A most preferred c-Met targeting peptide is:

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys.

Vectors suitable for guanylyl cyclase C targeting are known in the art, and are typically based on peptide analogues of E. coli heat-stable enterotoxin (ST peptides). Vectors suitable for IGF1R targeting have been described by Clemmons [Nature Rev. Drug Disc., 6, 821-833 (2006)].

In step (iv), the appropriate targeted therapy is any known to have an upstream or downstream effect on Her2, cMet, guanylyl cyclase C or IGF1R respectively. Chemotherapy with cytotoxic agents is a possible such therapy, and suitable such cytotoxic agents include: 5-fluorouracil, cisplatin, bleomycin, mitomycin, doxorubicin, methotrexate, topotecan, paclitaxel, vinorelbine or docetaxel. Such cytotoxic drugs can be used in combinations thereof such as cisplatin/5-fluorouracil (5-FU); carboplatin/paclitaxel or cisplatin/irinotecan. The cytotoxic drugs can also potentially be used in combination with the specific therapies described below.

When a Her2-targeting imaging agent finds abnormal uptake, preferred therapies for step (iv)(a) include treatment with Herceptin™ (Trastuzumab), which is a well-accepted Her2 targeting drug with proven efficacy [UK National Cancer Research Institute Clinical Guidelines; Bohme "Anti-HER2 therapy: How to use Herceptin in clinical practice". Eur. J. Oncol. Nursing, 4, 30-36 (2000)].

When a cMet-targeting imaging agent finds abnormal uptake, preferred therapies for step (iv)(b) are known and include treatment with the small molecule inhibitor PHA665752, as described by Watson et al [Neoplasia, 8, 949-955 (2006)].

When a GCC-targeting imaging agent finds abnormal uptake, preferred therapies for step (iv)(c) include those already developed in the context of GCC as a marker of colon cancer. Thus, eg. Waldman et al describe a GCC-targeted therapy based on ST peptides and thermal ablation ["Opportunities for near-infrared thermal ablation of colorectal metastases by guanylyl cyclase C-targeted gold nanoshells" Future Oncology 2, 705-716 (2006)]. Thermal ablation has been widely discussed as a possible treatment for Barrett's patients, and is thus believed to represent a viable therapy option there also.

When an IGF1R-targeting imaging agent finds abnormal uptake, preferred therapies for step (iv)(d) include known treatments directed at IGF1R as a target in cancer therapy. These are described by: Tao et al ["Mechanisms of Disease: Signaling of the insulin-like growth factor 1 receptor pathway—Therapeutic perspectives in cancer" Nat. Clin. Pract. Oncol. 4, 591-602 (2007)]; Shao et al ["Integrated molecular targeting of IGF1R and HER2 surface receptors and destruction of breast cancer cells using single wall carbon nanotubes" Nanotechnology, 18, 315101 (2007)]; Martins et al ["Insulin-like growth factor I receptor pathway inhibition by ADW742, alone or in combination with imatinib, doxorubicin, or vincristine, is a novel therapeutic approach in Ewing tumor" Clin. Cancer Res. 12, 3532-3540 (2006)]; Bohula et al ["Targeting the type 1 insulin-like growth factor receptor as anti-cancer treatment" Anti-Cancer Drugs 14, 669-682 (2003)]. Additional cancer therapeutic approaches using kinase inhibitors or monoclonal antibodies are described by Wang et al [Rec. Result. Cancer Res., 172, 59-76 (2007)].

The targeted therapy of step (iv) can be delivered by conventional routes of patient administration, such as intravenous, oral or topical (eg. by spraying onto the oesophagus), as is known in the art. Methods of formulating drugs for more efficient delivery to the oesophagus are known in the art [Batchelor, Pharmaceut. Res., 22(2), 175-181 (2005) and Collaud et al, J. Control. Rel., 123, 203-210 (2007)], and hence the treatments of step (iv) of the present invention may optionally be delivered via such formulations.

The imaging agent of step (i) can be delivered by conventional routes of patient administration, such as intravenous or oral, as is known in the art. When the imaging moiety is a radioisotope, the imaging agent is preferably administered via the intravenous route, since patient and operator radiation dose can be controlled more carefully that way. When the imaging moiety is an optical reporter the intravenous or oral administration route can be used. As noted above, methods of formulating drugs for more efficient oral delivery to the oesophagus, giving longer topical oesophageal contact times are known in the art, hence the optical imaging agent of step (i) of the present invention may optionally be delivered via such formulations.

The "different therapy" of step (v) is a new treatment or course of treatment for the individual patient, i.e. a treatment that the patient has not previously received. The 'different therapy' may be chosen from one of the remaining targeted therapy options (a) to (d) of step (iv), which was not determined to be unsuitable under step (v). This could include surgery and palliative care.

Preferred Aspects.

The method of the first aspect is preferably carried out using in vivo imaging, and hence a reporter suitable for in vivo imaging. The protein marker of step (i) is preferably chosen from Her2 and cMet, and is most preferably Her2. When the marker is Her2, a preferred therapy is Herceptin™. The abnormal uptake of step (iii) is preferably elevated uptake, since that is expected to give higher uptake of the imaging agent compared to tissue background, and thus facilitate detection by "hot spots".

The imaging moiety is preferably an optical reporter, for both in vitro and in vivo imaging approaches, more preferably a fluorescent near-infrared dye. The optical reporter is preferably also biocompatible, i.e. suitable for in vivo optical imaging. By the term "biocompatible" is meant is meant non-toxic and hence suitable for administration to the mammalian body, especially the human body without adverse reaction, or pain or discomfort on administration. Such NIR dyes suitably have their absorption maximum in the red to near-infrared wavelength 600-1200 nm. The NIR dye is preferably a cyanine dye.

The NIR dye is preferably a cyanine dye or benzopyrylium dye. Preferred cyanine dyes which are fluorophores are of Formula I:

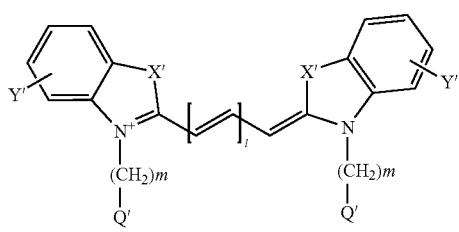

(I)

wherein:
each X' is independently selected from: —C(CH$_3$)$_2$, —S—, —O— or
—C[(CH$_2$)$_a$CH$_3$][(CH$_2$)$_b$M]-, wherein a is an integer of value 0 to 5, b is an integer of value 1 to 5, and M is group G or is selected from SO$_3$M$^1$ or H;

each Y' independently represents 1 to 4 groups selected from the group consisting of:
H, —CH$_2$NH$_2$, —SO$_3$M$^1$, —CH$_2$COOM$^1$, —NCS, F and a group G, and wherein the Y' groups are placed in any of the positions of the aromatic ring;

Q' is independently selected from the group consisting of: H, SO$_3$M$^1$, NH$_2$, COOM$^1$, ammonium, ester groups, benzyl and a group G;

M$^1$ is H or B$^c$; where B$^c$ is a biocompatible cation;

l is an integer from 1 to 3;

and m is an integer from 1 to 5;

wherein at least one of X', Y' and Q' comprises a group G;

G is a reactive or functional group suitable for attaching the dye to the vector via a covalent bond.

By the term "biocompatible cation" (B$^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

The G group reacts with a complementary group of the vector forming a covalent linkage between the cyanine dye fluorophore and the vector. G may be a reactive group that may react with a complementary functional group of the peptide, or alternatively may include a functional group that may react with a reactive group of the vector. Examples of reactive and functional groups include: active esters; isothiocyanate; maleimide; haloacetamide; acid halide; hydrazide; vinylsulphone; dichlorotriazine; phosphoramidite; hydroxyl; amino; sulphydryl; carbonyl; carboxylic acid and thiophosphate. Preferably G is an active ester.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NHS), sulpho-succinimidyl ester, pentafluorophenol, pentafluorothiophenol, para-nitrophenol, hydroxybenzotriazole and PyBOP (ie. benzotriazol-1-yl-oxytripyrrolidinophosphonium hexafluorophosphate). Preferred active esters are N-hydroxysuccinimide or pentafluorophenol esters, especially N-hydroxysuccinimide esters.

Cyanine dyes which are more preferred are of Formula Ia:

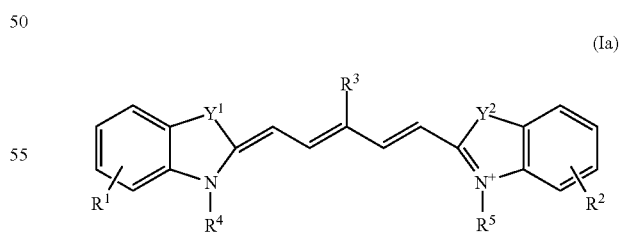

(Ia)

where:
Y$^1$ and Y$^2$ are independently —O—, —S—, —NR$^6$— or —CR$^7$R$^8$— and are chosen such that at least one of Y$^1$ and Y$^2$ is —CR$^7$R$^8$—;
R$^1$ and R$^2$ are independently H, —SO$_3$M$^1$ or R$^a$;
R$^3$ is H, C$_{1-5}$ alkyl, C$_{1-6}$ carboxyalkyl or an R$^a$ group;
R$^4$ to R$^6$ are independently C$_{1-5}$; alkyl, C$_{1-6}$, carboxyalkyl or R$^a$;

$R^7$ is H or $C_{1-3}$ alkyl;

$R^8$ is $R^a$ or $C_{1-6}$ carboxyalkyl;

$R^a$ is independently $C_{1-4}$ sulfoalkyl;

where $M^1$ is as defined in Formula I;

with the proviso that the cyanine dye of Formula Ia comprises at least one $R^a$ group and a total of 1 to 6 sulfonic acid substituents from the $R^1$, $R^2$ and $R^a$ groups.

By the term "sulfonic acid substituent" is meant a substituent of formula —$SO_3M^1$, where $M^1$ is as defined above. Preferred dyes of Formula Ia have 3 to 6 sulfonic acid substituents. The —$SO_3M^1$ substituent is covalently bonded to a carbon atom, and the carbon atom may be aryl (such as the $R^1$ or $R^2$ groups), or alkyl (ie. an $R^a$ group). In Formula Ia, the $R^a$ groups are preferably of formula —$(CH_2)_k SO_3M^1$, where $M^1$ is as defined above, and k is an integer of value 1 to 4. k is preferably 3 or 4.

Particularly preferred cyanine dyes are of Formula Ib:

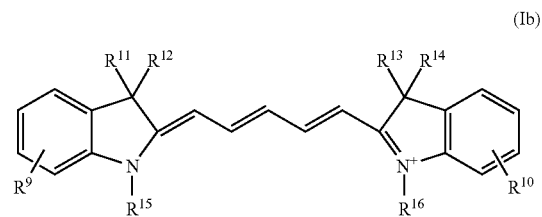

(Ib)

where:

$R^9$ and $R^{10}$ are independently H or $SO_3M^1$, and at least one of $R^9$ and $R^{10}$ is $SO_3M^1$;

$R^{11}$ and $R^{12}$ are independently $C_{1-4}$ alkyl or $C_{1-6}$ carboxyalkyl;

$R^{13}$, $R^{14}$, $R^{15}$ and $R^{16}$ are independently $R^b$ groups;

wherein $R^b$ is $C_{1-4}$ alkyl, $C_{1-6}$ carboxyalkyl or —$(CH_2)_q SO_3M^1$, where q is an integer of value 3 or 4;

where $M^1$ is as defined for Formulae I and Ia;

with the proviso that the cyanine dye has a total of 1 to 4 $SO_3M^1$ substituents in the $R^9$, $R^{10}$ and $R^b$ groups.

Preferred cyanine dyes of Formula Ib are chosen such that at least one $C_{1-6}$ carboxyalkyl group is present, in order to facilitate conjugation to the vector.

Preferred individual cyanine dyes of Formula Ib are summarised in Table 1:

TABLE 1 chemical structures of individual cyanine dyes.

| | Dye name | | | |
|---|---|---|---|---|
| | Cy5(1) | Cy5(2) | Cy5** | Alexa647 |
| $R^9$ | H | $SO_3H$ | $SO_3H$ | $SO_3H$ |
| $R^{10}$ | $SO_3H$ | $SO_3H$ | $SO_3H$ | $SO_3H$ |
| $R^{11}$ | $CH_3$ | $CH_3$ | $CH_3$ | $R^f$ |
| $R^{12}$ | $CH_3$ | $CH_3$ | $CH_3$ | $CH_3$ |
| $R^{13}$ | $CH_3$ | $CH_3$ | $CH_3$ | $CH_3$ |
| $R^{14}$ | $CH_3$ | $CH_3$ | —$(CH_2)_4SO_3H$ | $CH_3$ |
| $R^{15}$ | $R^f$ | $R^f$ | $R^f$ | —$(CH_2)_3SO_3H$ |
| $R^{16}$ | $CH_3$ | Et | —$(CH_2)_4SO_3H$ | —$(CH_2)_3SO_3H$ | where $R^f$ = —$(CH_2)_5COOH$.

Especially preferred cyanine dyes are of Formula Ic:

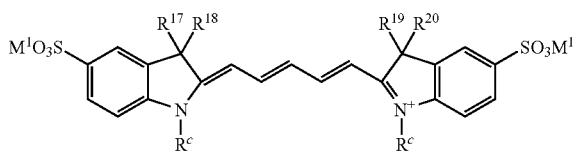

(Ic)

where:

$R^c$ is independently an $R^a$ group or $C_{1-6}$ carboxyalkyl;

$R^{17}$ to $R^{20}$ are independently $C_{1-5}$ alkyl or an $R^c$ group, and are chosen such that either $R^{17}$=$R^{18}$=$R^c$ or $R^{19}$=$R^{20}$=$R^d$, where $R^d$ is $C_{1-2}$ alkyl;

$R^a$ and $M^1$ are as defined above for Formula I.

Especially preferred cyanine dyes of Formulae Ib and Ic are Cy5 and Alexa647, with Cy5 being the ideal.

The term "benzopyrylium dye" has its conventional meaning. Suitable benzopyrylium dyes of the present invention are denoted $Bzp^M$ and are of Formula II:

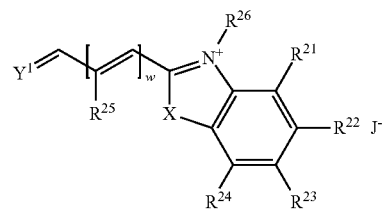

(II)

where:

$Y^1$ is a group of Formula $Y^a$ or $Y^b$

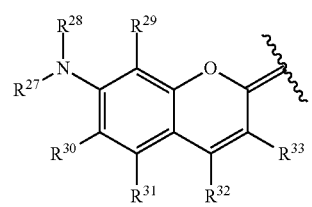

($Y^a$)

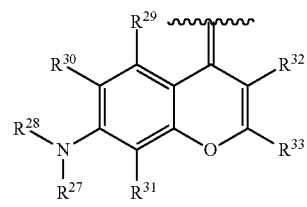

($Y^b$)

$R^{21}$-$R^{24}$ and $R^{29}$-$R^{33}$ are independently selected from H, —$SO_3M^1$, Hal, $R^g$ or $C_{3-12}$ aryl;

$R^{25}$ is H, $C_{1-4}$ alkyl, $C_{1-6}$ carboxyalkyl, $C_{3-12}$ arylsulfonyl, Cl, or $R^{25}$ together with one of $R^{26}$, $R^{34}$, $R^{35}$ or $R^{36}$ may optionally form a 5- or 6-membered unsaturated aliphatic, unsaturated heteroaliphatic or aromatic ring;

$R^{26}$ and $R^{36}$ are independently $R^g$ groups;

$R^{27}$ and $R^{28}$ are independently $C_{1-4}$ alkyl, $C_{1-4}$ sulfoalkyl or $C_{1-6}$ hydroxyalkyl or optionally together with one or both of $R^{29}$ and/or $R^{30}$ may form a 5- or 6-membered N-containing heterocyclic or heteroaryl ring;

X is —$CR^{34}R^{35}$, —O—, —S—, —Se—, —$NR^{36}$— or —CH═CH—, where $R^{34}$ to $R^{36}$ are independently $R^g$ groups;

$R^g$ is $C_{1-4}$ alkyl, $C_{1-4}$ sulfoalkyl, $C_{1-6}$ carboxyalkyl or $C_{1-6}$ hydroxyalkyl;

w is 1 or 2;

J is a biocompatible anion;

where $M^1$ is as defined for Formula I;

with the proviso that $Bzp^M$ comprises at least one sulfonic acid substituent chosen from the $R^{21}$ to $R^{36}$ groups.

By the term "biocompatible anion" (J) is meant a negatively charged counterion which forms a salt with an ionised, positively charged group (in this case an indolinium group), where said negatively charged counterion is also non-toxic and hence suitable for administration to the mammalian body, especially the human body. The counterion (J⁻) represents an anion which is present in a molar equivalent amount, thus balancing the positive charge on the $Bzp^M$ dye. The anion (J) is suitably singly- or multiply-charged, as long as a charge-balancing amount is present. The anion is suitably derived from an inorganic or organic acid. Examples of suitable anions include: halide ions such as chloride or bromide; sulphate; nitrate; citrate; acetate; phosphate and borate. A preferred anion is chloride.

The benzopyrylium dye ($Bzp^M$) of Formula II is a fluorescent dye or chromophore which is capable of detection either directly or indirectly in an optical imaging procedure using light of green to near-infrared wavelength (500-1200 nm, preferably 550-1000 nm, more preferably 600-800 nm). Preferably, the $Bzp^M$ has fluorescent properties.

Suitable imaging agents of the invention are those wherein the $Bzp^M$ is of Formula IIa or IIb:

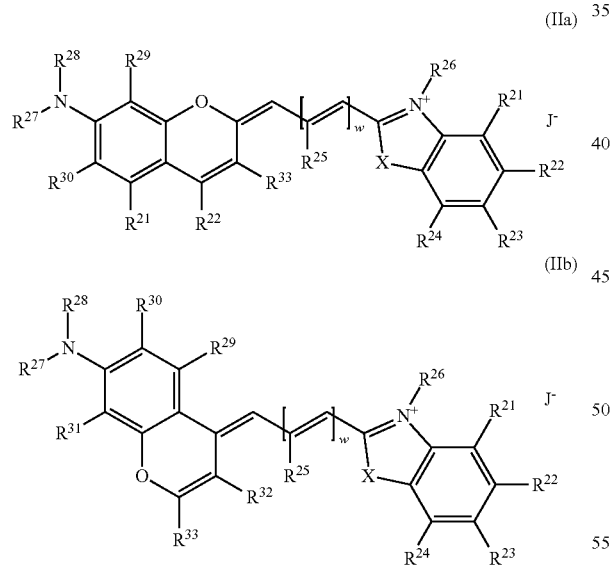

where X, w, J and $R^{21}$-$R^{33}$ are as defined for Formula II.

When $R^{25}$ together with one of $R^{26}$/$R^{34}$-$R^{36}$ forms a 5- or 6-membered unsaturated aliphatic, unsaturated heteroaliphatic or aromatic ring, suitable such aromatic rings include: phenyl, furan, thiazole, pyridyl, pyrrole or pyrazole rings. Suitable unsaturated rings comprise at least the C═C to which $R^{25}$ is attached.

When $R^{27}$ and/or $R^{28}$ together with one or both of $R^{29}$ and/or $R^{30}$ form a 5- or 6-membered N-containing heterocyclic or heteroaryl ring, suitable such rings include: thiazole, pyridyl, pyrrole or pyrazole rings or partially hydrogenated versions thereof preferably pyridyl or dihydropyridyl.

Preferred Features of the Benzopyrylium Dye.

The vector is preferably attached at positions $R^{25}$, $R^{26}$, $R^{34}$, $R^{35}$ or $R^{36}$ of the $Bzp^M$ of Formula II, more preferably at $R^{26}$, $R^{34}$, $R^{35}$ or $R^{36}$ most preferably at $R^{26}$, $R^{34}$ or $R^{35}$.

In order to facilitate the attachment the relevant $R^{25}$, $R^{26}$, $R^{34}$, $R^{35}$ or $R^{36}$ substituent is preferably $C_{1-6}$ carboxyalkyl, more preferably $C_{3-6}$ carboxyalkyl.

The benzopyrylium dye ($Bzp^M$) preferably has at least 2 sulfonic acid substituents, more preferably 2 to 6 sulfonic acid substituents, most preferably 2 to 4 sulfonic acid substituents. Preferably, at least one of the sulfonic acid substituents is a $C_{1-4}$ sulfoalkyl group. Such sulfoalkyl groups are preferably located at positions $R^{26}$, $R^{27}$, $R^{28}$, $R^{34}$, $R^{35}$ or $R^{36}$; more preferably at $R^{26}$, $R^{27}$, $R^{28}$, $R^{34}$ or $R^{35}$; most preferably at $R^{26}$ together with one or both of $R^{27}$ and $R^{28}$ of Formula II. The sulfoalkyl groups of Formula II, are preferably of formula —$(CH_2)_k SO_3 M^1$, where $M^1$ is H or $B^c$, k is an integer of value 1 to 4, and $B^c$ is a biocompatible cation (as defined above). k is preferably 3 or 4.

In Formula II, w is preferably 1. $R^{25}$ is preferably H or $C_{1-4}$ carboxyalkyl, and is most preferably H. X is preferably —$CR^{34}R^{35}$— or —$NR^{36}$—, and is most preferably —$CR^{34}R^{34}R^{35}$—.

Preferred $Bzp^M$ dyes are of Formula III:

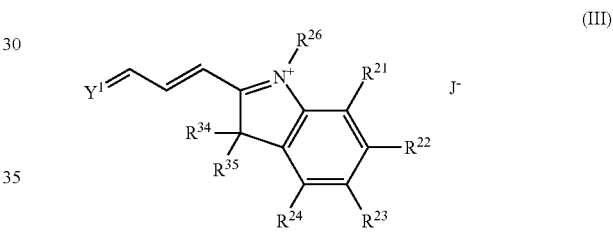

where $Y^1$, $R^{21}$-$R^{24}$, $R^{26}$, $R^{34}$, $R^{35}$ and J are as defined for Formula II.

Suitable dyes of Formula III are of Formula IIIa or IIIb:

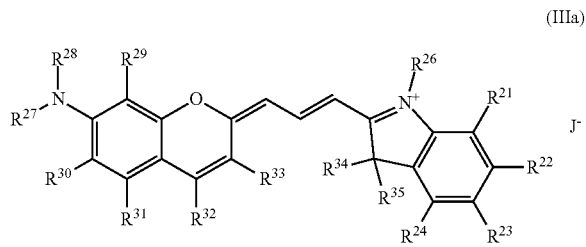

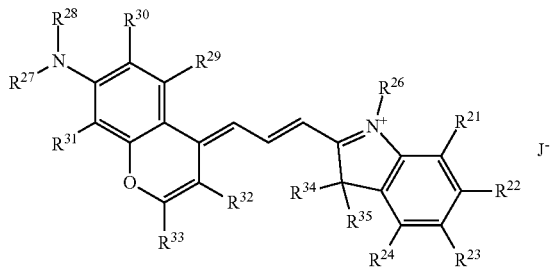

Preferred $R^{21}$-$R^{24}$ and $R^{26}$-$R^{33}$ groups of Formulae III, IIIa and IIIb are as described above for formulae II and IIb. In Formulae III, IIIa and IIIb, $R^{34}$ and $R^{35}$ are preferably chosen such that one is an $R^j$ group and the other is an $R^k$ group. $R^j$ is $C_{1-2}$ alkyl, most preferably methyl. $R^k$ is $C_{1-4}$ alkyl, $C_{1-6}$ carboxyalkyl or $C_{1-4}$ sulfoalkyl, preferably $C_{3-6}$ carboxyalkyl or $-(CH_2)_kSO_3M^1$ where k is chosen to be 3 or 4.

Preferably the dyes of Formula III have a $C_{1-6}$ carboxyalkyl substituent to permit facile covalent attachment to the vector.

In Formula II or III, when $R^{27}$ and/or $R^{28}$ together with one or both of $R^{29}$ and/or $R^{30}$ form a 5- or 6-membered N-containing heterocyclic or heteroaryl ring, preferred such rings are pyridyl or dihydropyridyl. A preferred such $Y^1$ group wherein an $R^{28}$ group has been cyclised with $R^{30}$ is of Formula $Y^c$:

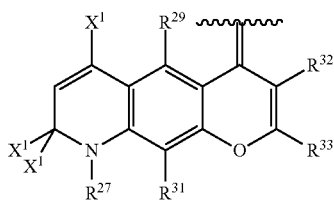

A preferred such $Y^1$ group wherein both $R^{27}$ and $R^{28}$ group have been cyclised is of Formula $Y^d$:

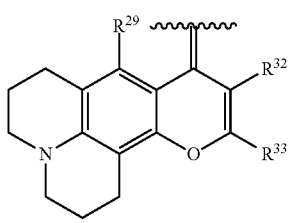

where:
$R^{27}$, $R^{29}$ and $R^{31}$-$R^{33}$ are as defined above;
each $X^1$ is independently H or $C_{1-4}$ alkyl.

In Formula $Y^c$, it is preferred that:
each $X^1$ is $CH_3$;
$R^{29}=R^{34}=H$;
$R^{32}$ is H;
$R^{33}$ is $CH_3$ or $-C(CH_3)_3$, more preferably $-C(CH_3)_3$.

In Formula $Y^d$, it is preferred that:
$R^{29}=H$;
$R^{32}$ is H;
$R^{33}$ is preferably $CH_3$ or $-C(CH_3)_3$, more preferably $-C(CH_3)_3$.

It is preferred that the $-NR^{27}R^{28}$ group of Formula II is either:
(i) in open chain form, ie. the $R^{27}/R^{28}$ groups are not cyclised with one or both of $R^{29}/R^{30}$. Preferred such $R^{27}$ and $R^{28}$ groups are independently chosen from $C_{1-4}$ alkyl or $C_{1-4}$ sulfoalkyl, most preferably ethyl or $C_{3-4}$ sulfoalkyl;
(ii) cyclised to give a cyclic $Y^1$ substituent of Formula $Y^c$ or $Y^d$, more preferably of Formula $Y^c$.

The open chain form (i) is most preferred.

Especially preferred dyes of Formula III are of Formula IIIc, IIId or IIIe:

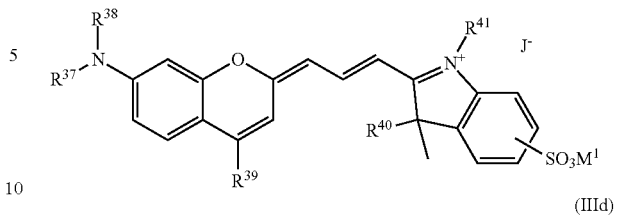

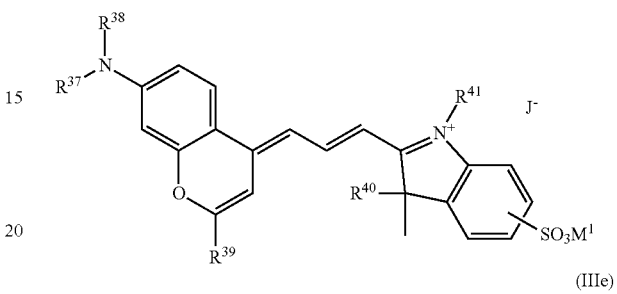

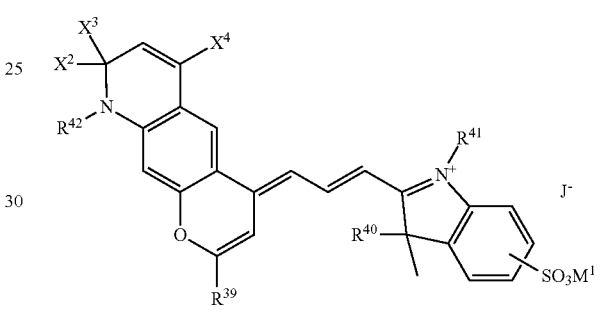

where:
$M^1$ and J are as defined above;
$R^{37}$ and $R^{38}$ are independently chosen from $C_{1-4}$ alkyl or $C_{1-4}$ sulfoalkyl;
$R^{39}$ is H or $C_{1-4}$ alkyl;
$R^{40}$ is $C_{1-4}$ alkyl, $C_{1-4}$ sulfoalkyl or $C_{1-6}$ carboxyalkyl;
$R^{41}$ is $C_{1-4}$ sulfoalkyl or $C_{1-6}$ carboxyalkyl;
$R^{42}$ is $C_{1-4}$ alkyl, $C_{1-4}$ sulfoalkyl or $C_{1-6}$ carboxyalkyl;
$X^2$, $X^3$ and $X^4$ are independently H or $C_{1-4}$ alkyl.

The dyes of Formulae IIId, IIIe and IIIf are preferably chosen such that one or more of $R^{40}$-$R^{42}$ is $C_{1-4}$ sulfoalkyl.

Preferred specific dyes of Formula IIId are DY-631 and DY-633:

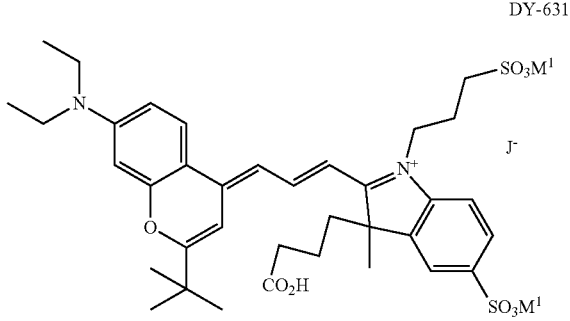

-continued

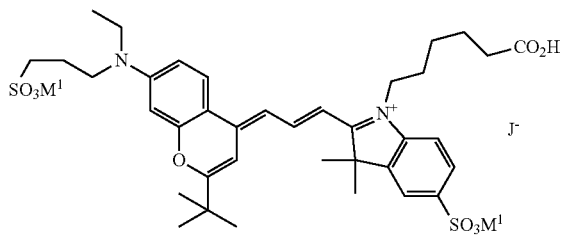

DY-633

A preferred specific dye of Formula IIIe is DY-652:

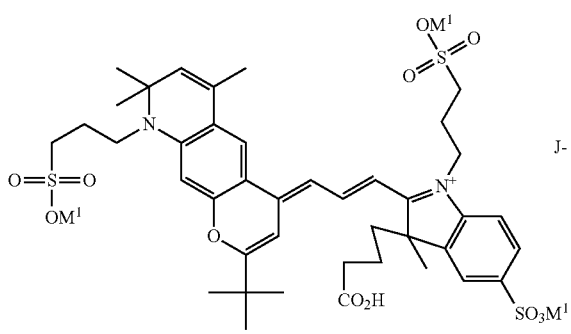

DY-652

Preferred specific benzopyrylium dyes are DY-631 and DY-652, with DY-652 being most preferred.

The method of the first aspect is expected to be particularly useful when the patient has been previously diagnosed to be suffering from dysplasia in Barrett's oesophagus., particularly high grade dysplasia patients (who are at a higher risk of developing cancer, and under current guidelines are referred for complete removal of diseased tissue). The different therapy of step (v) is preferably chosen from: chemotherapy with proton pump inhibitors, endoscopic mucosal ablation or surgical resection.

The method is also particularly useful when the patient has already failed to respond to a first-line therapy—i.e. is a "non-responder". That lack of response would typically be determined by follow-up endoscopy (see FIG. 1), In that case the first-line therapy would typically be one or more of: anti-reflux medication, endoscopic mucosal ablation and surgical resection, and the method is thus directed at finding the most appropriate second-line therapy.

The imaging agent of step (i) is preferably provided as a pharmaceutical composition. Such compositions comprise the imaging agent, together with a biocompatible carrier, in a form suitable for mammalian administration. The "biocompatible carrier" is a fluid, especially a liquid, in which the imaging agent can be suspended or dissolved, such that the composition is physiologically tolerable, ie. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection or isotonic saline.

The imaging agent and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. Preferred multiple dose containers comprise a single bulk vial (e.g. of 10 to 30 $cm^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may optionally contain additional excipients such as an antimicrobial preservative, pH-adjusting agent, filler, stabiliser or osmolality adjusting agent. By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The pharmaceutical compositions may be prepared under aseptic manufacture (ie. clean room) conditions to give the desired sterile, non-pyrogenic product. It is preferred that the key components, especially the associated reagents plus those parts of the apparatus which come into contact with the imaging agent (eg. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

The pharmaceutical compositions may also be prepared from a kit.

The method of the first aspect preferably further comprises the step:

(vi) when a targeted therapy as defined in (a)-(d) of step (iv) is initiated, use of the imaging agent of step (ii) to monitor the efficacy of said initiated therapy.

In that way, since the imaging agent targets the same protein marker as the therapy/chemotherapy, it is expected to be best-suited to the determination of whether abnormal expression of the target persists, and hence an objective measure of the effectiveness of the therapy.

Suitable vectors for the method of the invention are known in the literature, or in some cases commercially available—as described above. The synthesis of ST peptides and their conjugation with chelators for radiolabelling with $^{111}$In and $^{99m}$Tc for radiopharmaceutical imaging has been described [Cuthbertson et al., Tet. Lett., 42. 9257-59 (2000); Wolfe et al, J. Nucl. Med., 43, 392-399 (2002); Giblin et al, Bioconj. Chem., 15, 872-880 (2004)]. Radiolabelled Affibodies for Her2 imaging have been described by Engfeldt et al [Eur. J. Nucl. Med. Mol. Imaging, 34, 722-733 (2007); Cancer Res., 67, 2178-2186 (2007); Bioconj. Chem., 18, 549-558 and 1956-1964 (2007)].

When the imaging moiety comprises a radioactive isotope of fluorine (eg. $^{18}$F), the radioactive atom may be carried out via direct labelling using the reaction of $^{18}$F-fluoride with a suitable precursor having a good leaving group, such as an alkyl bromide, alkyl mesylate or alkyl tosylate. $^{18}$F can also be introduced by N-alkylation of amine precursors with alkylating agents such as $^{18}$F(CH$_2$)$_3$OMs (where Ms is mesylate) to give N—(CH$_2$)$_3$$^{18}$F, or O-alkylation of hydroxyl groups with $^{18}$F(CH$_2$)$_3$OMs or $^{18}$F(CH$_2$)$_3$Br. $^{18}$F can also be introduced by alkylation of N-haloacetyl groups with a $^{18}$F(CH$_2$)$_3$OH reactant, to give —NH(CO)CH$_2$O(CH$_2$)$_3$$^{18}$F derivatives. For aryl systems, $^{18}$F-fluoride nucleophilic displacement from an aryl diazonium salt, aryl nitro compound or an aryl quaternary ammonium salt are possible routes to aryl-$^{18}$F derivatives. Further details of synthetic routes to $^{18}$F-labelled and $^{123}$I-labelled derivatives are described by Bolton, J. Lab. Comp. Radiopharm., 45, 485-528 (2002).

Optical reporters can be conjugated to vectors by conventional methods—see Achilefu [Technol. Cancer. Res. Treat., 3, 393-409 (2004)], Li et al [Org. Lett., 8(17), 3623-26 (2006) and Bullok et al, [J. Med. Chem., 48, 5404-5407 (2005)]. Conjugation of a cyanine dye with a c-Met targeting peptide is also provided as Example 7 (see below).

In a second aspect, the present invention provides the use of the labelled vector as defined in the first aspect, in the manufacture of an imaging agent for use in the method of the first aspect. Preferred aspects of the vector and imaging agent are as described in the first aspect.

In a third aspect, the present invention provides the use of imaging agent as defined in the first aspect in the method of the first aspect. Preferred aspects of the vector and imaging agent are as described in the first aspect.

The imaging agent may optionally be provided via a kit, as is known in the art.

The invention is illustrated by the following Examples. Example 1 provides the tissue microarray method of the invention. Example 2 demonstrates that cMet levels were low in normal tissue, and strongly upregulated in metaplastic, dysplastic and to a lesser extent carcinoma tissue. This expression profile cannot be connected to disease progression, as cMet was highly expressed in all Barrett's patients, regardless of progression to higher risk stages (dysplasia or adenocarcinoma). Example 2 does, however, show that imaging cMet is a good indicator that cMet-targeted therapy is appropriate.

Example 3 demonstrates that Her2 expression was minimal in squamous tissue, accompanied by strong staining in Barrett's and high grade dysplasia, weak staining in low grade dysplasia and variable staining intensity in adenocarcinoma samples. Of particular interest was that Her2 expression was higher in Barrett's tissue adjacent to low grade dysplasia (LGD), high grade dysplasia (HGD) or carcinoma. Staining intensity increased with the severity of the adjacent lesion, pointing to a possible link between Her2 and disease progression. Example 3 shows that imaging Her2 is a good indicator that Her2-targeted therapy is appropriate.

Example 4 demonstrates that IGF1-R exhibited low or no staining in squamous tissue, with increased expression in Barrett's, dysplasia and adenocarcinoma stages. Example 4 shows that imaging IGF1-R is a good indicator that IGF1-R-targeted therapy is appropriate.

Example 5 shows that, whilst Guanylyl cyclase c can be detected in squamous tissue, expression increases in subsequent stages, reaching 90-100% for low grade dysplasia and carcinoma. Example 3 shows that imaging GCC is a good indicator that GCC-targeted therapy is appropriate.

Example 6 provides the synthesis of a c-Met targeting peptide (Compound 1).

Example 7 provides a method of labeling the peptide of Example 6 with a cyanine dye.

ABBREVIATIONS

Conventional single letter or 3-letter amino acid abbreviations are used.

| | |
|---|---|
| Acm: | Acetamidomethyl |
| ACN: | Acetonitrile. |
| Boc: | tert-Butyloxycarbonyl |
| DCM: | Dichloromethane |
| DMSO: | Dimethylsulfoxide |
| HBTU: | O-Benzotriazol-1-yl-N,N,N',N'-tetramethyluronium hexafluorophosphate |
| HPLC: | High performance liquid chromatography |
| NHS: | N-hydroxy-succinimide |
| NMM: | N-Methylmorpholine |
| NMP: | 1-Methyl-2-pyrrolidinone |
| Pbf: | 2,2,4,6,7-Pentamethyldihydrobenzofuran-5-sulfonyl |
| tBu: | t-butyl |
| TFA: | Trifluoroacetic acid |
| TIS: | Triisopropylsilane |
| Trt: | Trityl |

Example 1

Tissue Microarray

Fresh biopsy tissue samples were collected from Barrett's oesophagus patients, having a range of histologies. There were 107 samples in total, comprising: 20 gastric controls; 7 squamous controls; 20 Barrett's metaplasia; 20 low-grade dysplasia; 20 high-grade dysplasia; and 20 adenocarcinomas. Tissue Microarray was carried on the above tissue samples, where each core had a diameter of ~0.6 mm with variable depth.

A protocol for Tissue Microarray is described by Camp et al ["Validation of tissue microarray technology in breast carcinoma". Lab. Invest. 80, 1943-1949 (2000)]. Full section slides were from the same paraffin blocks that the cores were obtained from. All tissue was from patient biopsies and no patients had had chemotherapy specifically for oesophageal dysplasia/adenocarcinoma.

The expression of the following biological markers was determined: Her2, (b) cMet, (c) guanylyl cyclase or (d) IGF1R, with the results described in Examples 2 to 5. Metaplasia refers to an abnormal change in the nature of the tissue (in oesophageal metaplasia, normal squamous epithelium is replaced by columnar epithelium), whereas dysplasia refers to abnormal tissue growth (in oesophageal dysplasia, the metaplastic columnar epithelium begins to lose control of proliferation).

Example 2 eMet Expression

C-met acts as a receptor for hepatocyte growth factor (HGF). The following antibodies were used in the immunohistochemical analysis:

R&D Systems Anti-human HGF R (c-Met) goat Antibody (AF276) 1:25 (used for TMA and full section staining);

Novocastra c-Met (HGF R) mouse monoclonal (8F11) (non specific staining).

Immunohistochemical analysis in a similar manner to Example 1, gave the results shown in (Table 1):

TABLE 1

| | | cMet strong staining % | | |
|---|---|---|---|---|
| Squamous | Barrett's metaplasia | Low-grade Dysplasia | High-grade Dysplasia | Adenocarcinoma |
| 0% (0/7) | 41% (7/17) | 50% (8/16) | 37.5% (6/16) | 18 (3/17) |

Example 3

Her2 Expression

CONFIRM™ anti-HER-2/neu (Ventana Medical Systems Inc, Tucson, Ariz., USA) antibody was used.

30 mg/mL rabbit monoclonal antibody clone 4B5 IgG1 with affinity to the COOH terminus of the HER2/neu protein. The results are shown in Table 2:

TABLE 2

| | | Her2 strong staining % | | |
|---|---|---|---|---|
| Squamous | Barrett's metaplasia (BM) | Low-grade Dysplasia | High-grade Dysplasia | Adenocarcinoma (Ad) |
| 0% (0/7) | 40% (4/10) | 20% (1/5) | 55% (5/9) | 20% (2/10) |
| | BM adj. LGD | | BM adj. HGD | BM adj. Ad |
| | 25% (2/8) | | 50% (3/6) | 83% (5/6) |

Where: Adj = adjacent.

Example 4

IGF1-R Expression

Insulin-related growth factor 1 receptor (IGF1-R) is a cellular receptor with tyrosine kinase activity, which also has mitogenic and tumourigenic properties. The antibody used was Chemicon mouse anti-insulin-like-growth factor-1 receptor monoclonal (MAB1120).

The results are shown in Table 3:

TABLE 3

| | | IGF-1R Strong Staining | | |
|---|---|---|---|---|
| Squamous | Barrett's metaplasia | Low-Grade Dysplasia | High-grade Dysplasia | Adenocarcinoma |
| 0% (0/15) | 41% (7/17) | 36% (4/11) | 67% (6/9) | 30% (6/9) |

Example 5

Guanylyl Cyclase C Expression

GC-C is a surface receptor specifically expressed by epithelial cells of the intestine.

The antibody used was Abgent GUCY2C rabbit polyclonal (AP7136a) 1:50.

The results are shown in Table 4:

TABLE 4

| | | GCC Strong Staining | | |
|---|---|---|---|---|
| Squamous | Barrett's metaplasia | Low-Grade Dysplasia | High-grade Dysplasia | Adenocarcinoma |
| 31%(4/13) | 50% (5/10) | 100% (2/2) | 63% (7/11) | 90% (9/10) |

Example 6

Synthesis of a c-Met Targeting Peptide (Compound 1)

Step (a): Synthesis of Protected Precursor Linear Peptide.

The precursor linear peptide has the structure:
Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$ The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-

Thr(ψ$^{Me,Me}$pro)-Glu(OtBu)-Gly-Thr(tBu)-Gly-Gly-Gly-Lys (Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 mm. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 30 min) of the crude peptide afforded 100 mg of pure Compound 1 linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenemenex Luna 3μ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge

Cys4-16; Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$.

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 44 min) of the residue afforded 72 mg of pure Compound I monocyclic precursor.

The pure product (as a mixture of isomers P1 to P3) was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 5.37 min (P1); 5.61 min (P2); 6.05 min (P3)). Further product characterisation was carried out using electrospray mass spectrometry (MH$_2^{2+}$ calculated: 1463.6, MH$_2^{2+}$ found: 1464.1 (P1); 1464.4 (P2); 1464.3 (P3)).

Step (c): Formation of Second Cys6-14 Disulfide Bridge (Compound 1)

The monocyclic precursor from step (b) (72 mg) was dissolved in 75% AcOH/water (72 mL) under a blanket of nitrogen. 1 M HCl (7.2 mL) and 0.05 M I$_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1% TFA (4 mL) and the product purified using preparative HPLC.

Purification by preparative HPLC (gradient: 0% B for 10 min, then 20-30% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 43-53 min) of the residue afforded 52 mg of pure Compound 1. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 6.54 min). Further product characterisation was carried out using electrospray mass spectrometry (MH$_2^{2+}$ calculated: 1391.5, MH$_2^{2+}$ found: 1392.5).

Example 7

Conjugation of a Cyanine Dye to Compound 1

Compound 1 (Example 6; 10 mg), NMM (4 μL) and Cy5 NHS ester (5.7 mg; GE Healthcare PA15104) were dissolved in NMP (1 mL) and the reaction mixture stirred for 7 hrs. The reaction mixture was then diluted with 5% acetonitrile/water (8 mL) and the product purified using preparative HPLC.

Purification by preparative HPLC (gradient: 5-50% B over 40 min where A=H$_2$O/0.1 HCOOH and B=ACN/0.1% HCOOH, flow rate: 10 mL/min, column: Phenomenex Luna 5μ C18 (2) 250×21.20 mm, detection: UV 214 nm, product retention time: 35.5 min) of the crude peptide afforded 8.1 mg of pure dye-conjugated product. The pure product was analysed by analytical HPLC (gradient: 5-50% B over 10 min where A=H$_2$O/0.1% HCOOH and B=acetonitrile/0.1% HCOOH, flow rate: 0.3 mL/min, column: Phenomenex Luna 3μ C18 (2) 50×2 mm, detection: UV 214 nm, product retention time: 8.15 min). Further product characterisation was carried out using electrospray mass spectrometry (MH$_2^{2+}$ calculated: 1710.6, MH$_2^{2+}$ found: 1711.0).

What is claimed is:

1. A method to assist in the determination of the most suitable course of therapy for an individual patient previously diagnosed to be suffering from Barrett's oesophagus, said method comprising:
   (i) providing to said patient a first imaging agent which comprises a vector which selectively targets a protein marker chosen from one of (a) Her2, (b) cMet, (c) guanylyl cyclase C or (d) IGF1R, and an imaging moiety chosen from a radioisotope or an optical reporter;
   (ii) imaging at least a portion of the oesophagus of said patient with said first imaging agent from step (i);
   (iii) making a determination from the imaging of step (ii) whether there is increased uptake of the imaging agent relative to background at one or more locations of the patient's oesophagus;
   (iv) when the determination of step (iii) shows increased uptake, treating the patient based on the protein marker of the imaging agent used in step (ii):
      (a) for Her2, treatment with a drug or therapy which targets Her2;
      (b) for cMet, treatment with a drug or therapy which targets cMet;
      (c) for guanylyl cyclase C, treatment with a drug or therapy which targets guanylyl cyclase C;
      (d) for IGF1R, treatment with a drug or therapy which targets IGF1R; and
   (v) when no increased uptake is detected in step (iii), either a different therapy is given to said patient, or steps (iii)-(v) are repeated for said patient with a second imaging agent which comprises a different vector to that employed in step (ii);

where the patient has already failed to respond to a first-line therapy from one or more of: anti-reflux medication, endoscopic mucosal ablation and surgical resection.

2. The method of claim 1, where the protein marker is chosen from Her2 and cMet.

3. The method of claim 2, where the protein marker is Her2.

4. The method of claim 1, where the imaging moiety is a radioisotope for PET external imaging of the human body or a radioisotope for SPECT external imaging of the human body.

5. The method of claim 1, where the imaging moiety is an optical reporter.

6. The method of claim 5, where the optical reporter is a dye having an absorption maximum in the red to near-infrared wavelength 600-1200 nm.

7. The method of claim 5, where the optical reporter is biocompatible.

8. The method of claim 1, where the patient is previously diagnosed to be suffering from dysplasia in Barrett's oesophagus.

9. The method of claim 1, where the different therapy of step (v) is chosen from: chemotherapy with proton pump inhibitors, endoscopic mucosal ablation or surgical resection.

10. The method of claim 1, where the different therapy of step (v) is chosen from one of the remaining targeted therapy options (a) to (d) of step (iv), which was not determined to be unsuitable under step (v).

11. The method of claim 1, where the imaging agent of step (i) is provided as a pharmaceutical composition.

12. The method of claim 1, further comprising the step:
   (vi) when a targeted therapy as defined in (a)-(d) of step (iv) is initiated, use of the imaging agent of step (ii) to monitor the efficacy of said initiated therapy.

* * * * *

SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence

```
<220> FEATURE:
<223> OTHER INFORMATION: Synthetic peptide
<220> FEATURE:
<221> NAME/KEY: residue
<222> LOCATION: (1)..(13)
<223> OTHER INFORMATION: cysteine residues at position 1 and 13 are
      cyclised to form a disulfide bond
<220> FEATURE:
<221> NAME/KEY: misc_feature
<222> LOCATION: (2)..(2)
<223> OTHER INFORMATION: X is Asn, His or Tyr
<220> FEATURE:
<221> NAME/KEY: residue
<222> LOCATION: (3)..(11)
<223> OTHER INFORMATION: cysteine residues at position 3 and 11 are
      cyclised to form a disulfide bond
<220> FEATURE:
<221> NAME/KEY: misc_feature
<222> LOCATION: (4)..(4)
<223> OTHER INFORMATION: X is Gly, Ser, Thr or Asn
<220> FEATURE:
<221> NAME/KEY: misc_feature
<222> LOCATION: (8)..(8)
<223> OTHER INFORMATION: X is Thr or Arg
<220> FEATURE:
<221> NAME/KEY: misc_feature
<222> LOCATION: (15)..(15)
<223> OTHER INFORMATION: X is Ala, Asp, Glu, Gly or Ser
<220> FEATURE:
<221> NAME/KEY: misc_feature
<222> LOCATION: (16)..(16)
<223> OTHER INFORMATION: X is Ser or Thr
<220> FEATURE:
<221> NAME/KEY: misc_feature
<222> LOCATION: (17)..(17)
<223> OTHER INFORMATION: X is Asp or Glu

<400> SEQUENCE: 1

Cys Xaa Cys Xaa Gly Pro Pro Xaa Phe Glu Cys Trp Cys Tyr Xaa Xaa
1               5                   10                  15

Xaa

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: residue
<222> LOCATION: (2)..(14)
<223> OTHER INFORMATION: cysteine residues at position 2 and 14 are
      cyclised to form a disulfide bond
<220> FEATURE:
<221> NAME/KEY: misc_feature
<222> LOCATION: (3)..(3)
<223> OTHER INFORMATION: X is Asn, His or Tyr
<220> FEATURE:
<221> NAME/KEY: residue
<222> LOCATION: (4)..(12)
<223> OTHER INFORMATION: cysteine residues at positions 4 and 12 are
      cyclised to form a disulfide bond
<220> FEATURE:
<221> NAME/KEY: misc_feature
<222> LOCATION: (5)..(5)
<223> OTHER INFORMATION: X is Gly, Ser, Thr or Asn
<220> FEATURE:
<221> NAME/KEY: misc_feature
<222> LOCATION: (9)..(9)
<223> OTHER INFORMATION: X is Thr or Arg
<220> FEATURE:
<221> NAME/KEY: misc_feature
<222> LOCATION: (16)..(16)
<223> OTHER INFORMATION: X is Ala, Asp, Glu, Gly or Ser
<220> FEATURE:
<221> NAME/KEY: misc_feature
<222> LOCATION: (17)..(17)
```

```
<223> OTHER INFORMATION: X is Ser or Thr
<220> FEATURE:
<221> NAME/KEY: misc_feature
<222> LOCATION: (18)..(18)
<223> OTHER INFORMATION: X is Asp or Glu

<400> SEQUENCE: 2

Ser Cys Xaa Cys Xaa Gly Pro Pro Xaa Phe Glu Cys Trp Cys Tyr Xaa
1               5                   10                  15

Xaa Xaa

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: residue
<222> LOCATION: (4)..(16)
<223> OTHER INFORMATION: cysteine residues at positions 4 and 16 are
      cyclised to form a disulfide bond
<220> FEATURE:
<221> NAME/KEY: misc_feature
<222> LOCATION: (5)..(5)
<223> OTHER INFORMATION: X is Asn, His or Tyr
<220> FEATURE:
<221> NAME/KEY: residue
<222> LOCATION: (6)..(14)
<223> OTHER INFORMATION: cysteine residues at 6 positions and 14 are
      cyclised to form a disulfide bond
<220> FEATURE:
<221> NAME/KEY: misc_feature
<222> LOCATION: (7)..(7)
<223> OTHER INFORMATION: X is Gly, Ser, Thr or Asn
<220> FEATURE:
<221> NAME/KEY: misc_feature
<222> LOCATION: (11)..(11)
<223> OTHER INFORMATION: X is Thr or Arg
<220> FEATURE:
<221> NAME/KEY: misc_feature
<222> LOCATION: (18)..(18)
<223> OTHER INFORMATION: X is Ala, Asp, Glu, Gly or Ser
<220> FEATURE:
<221> NAME/KEY: misc_feature
<222> LOCATION: (19)..(19)
<223> OTHER INFORMATION: X is Ser or Thr
<220> FEATURE:
<221> NAME/KEY: misc_feature
<222> LOCATION: (20)..(20)
<223> OTHER INFORMATION: X is Asp or Glu

<400> SEQUENCE: 3

Ala Gly Ser Cys Xaa Cys Xaa Gly Pro Pro Xaa Phe Glu Cys Trp Cys
1               5                   10                  15

Tyr Xaa Xaa Xaa Gly Thr
            20

<210> SEQ ID NO 4
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: residue
<222> LOCATION: (4)..(17)
<223> OTHER INFORMATION: cysteine residues at position 4 and 16 are
      cyclised to form a disulfide bond
<220> FEATURE:
<221> NAME/KEY: residue
<222> LOCATION: (6)..(14)
<223> OTHER INFORMATION: cysteine residues at positions 6 and 14 are
      cyclised to form a disulfide bond
```

```
<400> SEQUENCE: 4

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
            20                  25
```